United States Patent
Ross et al.

(10) Patent No.: US 6,814,699 B2
(45) Date of Patent: Nov. 9, 2004

(54) LIGHT SOURCE FOR BORESCOPES AND ENDOSCOPES

(75) Inventors: Ian Michael Ross, Essex (GB); Nicki John Paris, Essex (GB); Christopher Paul Robinson, Essex (GB)

(73) Assignee: Keymed (Medical & Industrial Equipment) Ltd., Essex (GB)

( * ) Notice: Subject to any disclaimer, the term of this patent is extended or adjusted under 35 U.S.C. 154(b) by 134 days.

(21) Appl. No.: 10/168,021

(22) PCT Filed: Dec. 28, 2000

(86) PCT No.: PCT/GB00/05008

§ 371 (c)(1),
(2), (4) Date: Jun. 18, 2002

(87) PCT Pub. No.: WO01/49164

PCT Pub. Date: Jul. 12, 2001

(65) Prior Publication Data

US 2002/0193664 A1 Dec. 19, 2002

(30) Foreign Application Priority Data

Dec. 29, 1999 (GB) .............................................. 9930781

(51) Int. Cl.⁷ .............................. A61B 1/07; G02B 6/32
(52) U.S. Cl. ...................... 600/179; 600/182; 600/177; 362/555; 362/574
(58) Field of Search ................................ 600/179, 178, 600/129, 182, 176, 177; 362/555, 574, 575, 572

(56) References Cited

U.S. PATENT DOCUMENTS

| | | | | | |
|---|---|---|---|---|---|
| 4,652,093 A | * | 3/1987 | Stephen et al. | ................ | 356/23 |
| H445 H | * | 3/1988 | Bock et al. | ................... | 264/1.7 |
| 4,774,434 A | * | 9/1988 | Bennion | ...................... | 313/500 |
| 5,241,170 A | | 8/1993 | Field, Jr. et al. | ............. | 250/214 |
| 5,363,135 A | * | 11/1994 | Inglese | ......................... | 348/70 |
| 5,371,384 A | * | 12/1994 | Wada | ........................... | 257/82 |
| 5,660,461 A | | 8/1997 | Ignatius et al. | ............. | 362/241 |
| 5,733,246 A | | 3/1998 | Forkey | ....................... | 600/160 |
| 5,908,294 A | * | 6/1999 | Schick et al. | ................. | 433/29 |
| 6,054,222 A | * | 4/2000 | Takami et al. | .............. | 428/417 |
| 6,110,106 A | | 8/2000 | MacKinnon et al. | ........ | 600/181 |
| 6,186,944 B1 | * | 2/2001 | Tsai | ........................... | 600/200 |
| 6,188,527 B1 | * | 2/2001 | Bohn | ......................... | 359/710 |
| 6,190,309 B1 | * | 2/2001 | Ooshima et al. | ........... | 600/179 |
| 6,217,512 B1 | * | 4/2001 | Salo et al. | .................. | 600/160 |

(List continued on next page.)

FOREIGN PATENT DOCUMENTS

| | | |
|---|---|---|
| DE | 298 05 624 | 7/1998 |
| GB | 2 276 032 | 9/1994 |
| JP | 60-88921 | * 5/1985 |
| JP | 11-267099 | * 10/1999 |
| WO | WO 95 15060 | 6/1995 |
| WO | WO 99/66830 | 12/1999 |

*Primary Examiner*—John P. Leubecker
(74) *Attorney, Agent, or Firm*—Smith, Gambrell & Russell, LLP

(57) ABSTRACT

The present invention provides an apparatus (24) for use as a borescope or endoscope for viewing an object at a remote or inaccessible location. The apparatus (24) comprises a tube (22) having a proximal end and a distal end and means in the tube for obtaining an image of an object and transmitting it to a viewing device. The apparatus (24) also comprises illumination means comprising an array (20) of light emitting diodes (10) mounted on a substrate (12) and covered by a common protective shield (18) of optically clear material. The array (20) may be mounted at the distal end of the tube (22) adjacent a viewing port (26). Alternatively, the array (20) may be mounted at the proximal end of the tube, adjacent the end face (38) of a bundle of optical fibers which transmit light to the distal end of the tube (22). The arrangement eliminates the need for an external light source ande light guide, thereby reducing light losses and making the apparatus more compact.

15 Claims, 6 Drawing Sheets

U.S. PATENT DOCUMENTS

| | | | |
|---|---|---|---|
| 6,260,994 B1 * | 7/2001 | Matsumoto et al. | 362/574 |
| 6,293,910 B1 * | 9/2001 | Yamakita et al. | 600/132 |
| 6,318,887 B1 * | 11/2001 | Matsumoto | 362/574 |
| 6,331,156 B1 * | 12/2001 | Haefele et al. | 600/179 |
| 6,438,302 B1 * | 8/2002 | Utsui et al. | 385/117 |
| 6,449,006 B1 * | 9/2002 | Shipp | 348/70 |
| 6,488,619 B1 * | 12/2002 | Miyanaga | 600/179 |
| 6,501,091 B1 * | 12/2002 | Bawendi et al. | 257/14 |
| 6,513,949 B1 * | 2/2003 | Marshall et al. | 362/231 |
| 6,577,332 B2 * | 6/2003 | Osawa et al. | 347/241 |

* cited by examiner

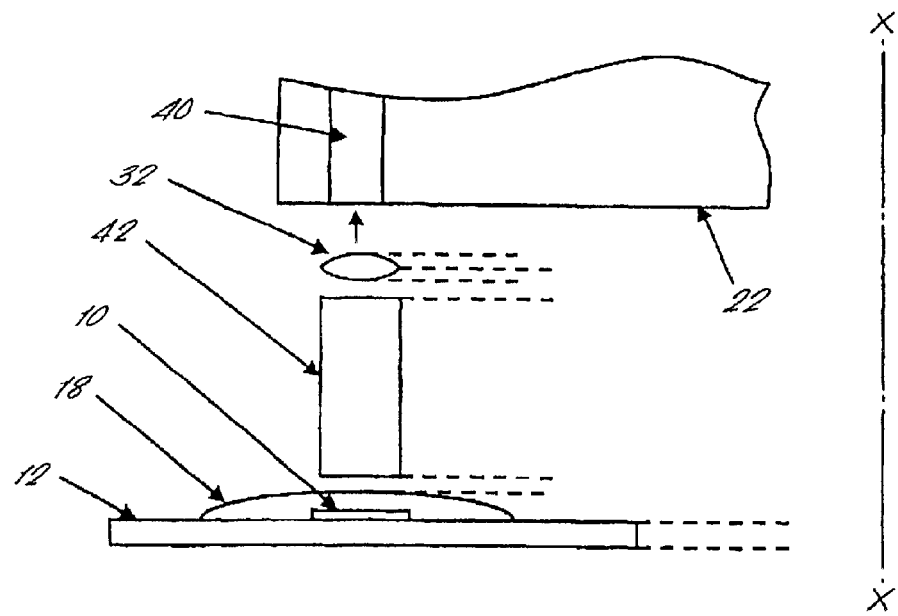
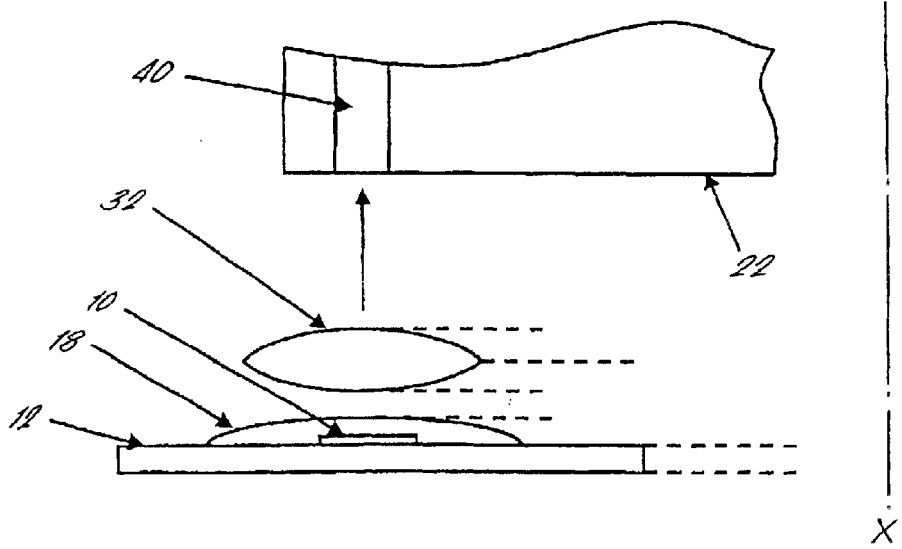

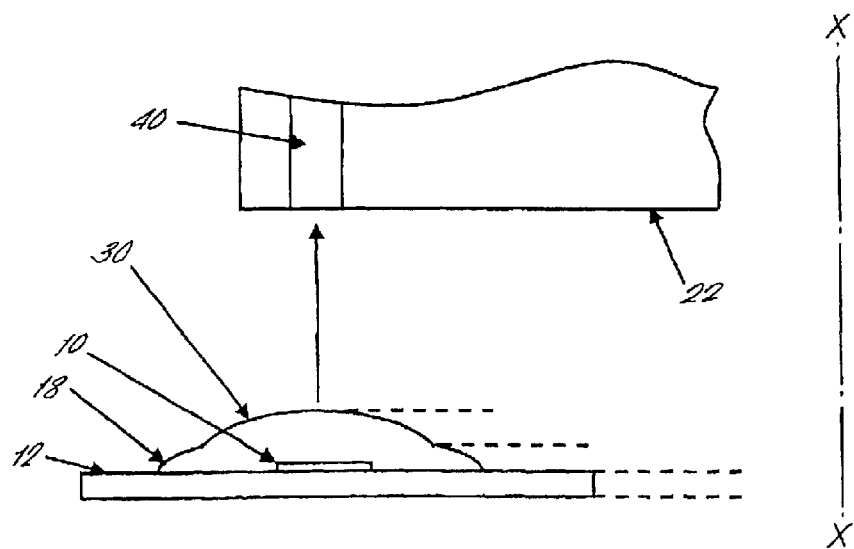

LIGHT SOURCE FOR BORESCOPES AND ENDOSCOPES

FIELD OF THE INVENTION

The present invention relates generally to borescopes and endoscopes, which are well-known optical devices for viewing objects at remote or inaccessible locations. Borescopes and endoscopes usually incorporate means to illuminate the field of view. This typically consists of a bundle of optical fibres for transmitting light from a light source, located externally of the device, through the device and out of an illumination port. The present invention relates to an improved means of providing illumination of the field of view.

SUMMARY OF THE INVENTION

Accordingly, the present invention provides an apparatus for use as a borescope or endoscope for viewing an object at a remote or inaccessible location, comprising a tube having a proximal end a distal end, means in the tube for obtaining an image of an object and transmitting it to a viewing device, and illumination means comprising an array of light emitting diodes (LEDs) mounted on a substrate and covered by a common protective shield of optically clear material.

In this way, an external light source and a conventional light guide for transmitting its light to a bundle of optical fibres in the tube is unnecessary. This greatly reduces the light losses, ensuring that more of the light from the light source is available to illuminate the field of view.

In one embodiment, the array of LEDs is positioned at the distal end of the tube adjacent a viewing port provided in the tube.

Alternatively, the illumination means further includes a plurality of optical fibres for transmitting light through the tube from the proximal end to the distal end, wherein the fibres are arranged in annular form and present an annular end face at the proximal end of the tube, wherein the array of LEDs is annular and is positioned at the proximal end of the tube facing the annular end face of the fibres.

In either embodiment, the protective shield may be shaped so as to form a lens to focus light produced by the LEDs.

Alternatively, a separate lens may be positioned in front of the array in order to focus light produced by the light emitting diodes.

If an annular array of light emitting diodes is used, an annular light pipe may be positioned between the array and the end face of the optical fibres for transmitting light from the array to the fibres.

In this case, the distal end of the light pipe may be shaped to form a lens to focus light onto the end face of the fibres.

Alternatively, a separate lens may be positioned between the light pipe and the end face of the optical fibres.

Cooling means may be provided to dissipate any heat produced by the array of LEDs.

The LEDs may emit white light. Alternatively, they may emit blue light, in which case the protective shield preferably incorporates white or yellow phosphor, whereby the array as a whole provides white light.

Alternatively, the array may comprise a plurality of differently coloured LEDs operable in combination to produced white light.

In particular, the array may comprise a mixture of LEDs operable to produce red, green or blue light and means to operate the LEDs so as to provide light which sequentially alternates between red, green and blue.

In further alternative embodiments, the LEDs may produce infra red light or ultraviolet light.

Preferably, the array includes at least fifty LEDs, and more preferably at least eighty LEDs.

If the array is provided at the proximal end of the tube, it may be incorporated in an assembly which is detachable from the tube.

BRIEF DESCRIPTION OF THE DRAWINGS

The invention will now be described in detail, by way of example only, with reference to the accompanying drawings in which:

FIG. 9 illustrates a cross sectional view of an eighth embodiment of the invention, with the array at the proximal end;

FIG. 10 illustrates a cross sectional view of a ninth embodiment of the invention, with the array at the proximal end;

FIG. 11 illustrates a cross sectional view of a tenth embodiment of the invention, with the array at the proximal end.

DETAILED DESCRIPTION

A typical borescope or endoscope comprises a tube, which may be rigid or flexible, having a distal end which is inserted in use into, for example, a machine or a human body. A viewing port is provided in the distal end of the tube through which an object may be viewed. An optical train may be provided in the tube for transferring an image of the object from the distal end to the proximal end. An ocular assembly at the proximal end focuses the image onto the eye of an observer or onto a camera attachment for display on a screen. Alternatively, an image to video conversion device, such as a CCD chip may be provided in the distal end of the tube, with appropriate wiring passing from the chip along the tube.

To enable viewing of the object, it is usually necessary to provide some form of illumination. Typically, this consists of a bundle of optical fibres running through the tube to an illumination port adjacent the viewing port.

In conventional borescopes or endoscopes, the bundle of optical fibres runs down one side of the insertion tube, with an optical train extending down the other side of the tube, both being eccentric to the longitudinal axis of the tube. An external light source is connected to the bundle of optical fibres by means of a light guide. In conventional orbital scan scopes in which the insertion tube is rotatable about its longitudinal axis, this arrangement can lead to misalignment of the light guide with the optical bundle during rotation.

The external light source is typically a conventional high wattage bulb producing very bright light and a light guide for transmitting this light into the scope and to the optical fibres. Because the bulb is linked to the optical fibres by a conventional light guide there can be light losses of up to 70%, dramatically reducing the illumination available at the distal end of the scope.

The present invention employs an alternative light source within the borescope or endoscope, to avoid the need for an external light source and light guide. In particular, the present invention employs a dense array of light emitting diodes (LEDs) as the light source.

Figure 1:
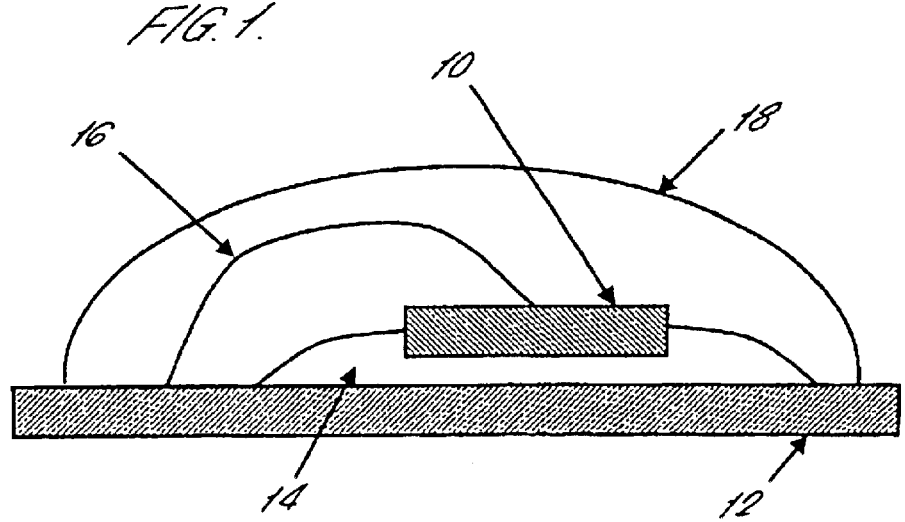
FIG. 1 illustrates in cross section part of an array of LEDs.

Conventionally, an LED is thought of as a tiny silicon chip with metal connections which is encapsulated in a clear epoxy substance to provide a lens. In the present invention, in order to increase the density of LEDs which can be mounted on a substrate, a stripped down version of an LED is used, as illustrated in FIG. 1. This is essentially the LED chip 10 without the epoxy encapsulation. These LED chips 10 are mounted on a ceramic substrate 12 by means of a thermally and electrically conductive glue 14 which serves as one of the connections for the LED chip 10. A gold bond wire 16 is attached to the top of each LED chip 10 and connected with gold circuit tracks (not shown) on the substrate 12 to provide the other connection for the LED chip 10.

A protective layer 18 of optically clear glue such as epoxy is then provided to cover all of the LED chips 10 mounted on the same substrate.

Figure 2:
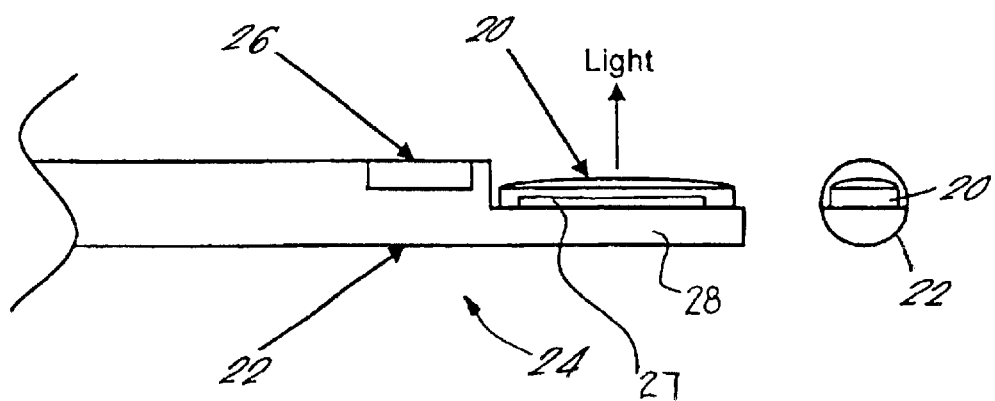
FIG. 2 illustrates a side and end view of a first embodiment of the invention including an array at the distal end of the borescope or endoscope.

A first embodiment of the present invention is shown in FIG. 2. Here, an array 20 of LED chips 10 is provided at the distal end of the insertion tube 22 of a borescope or endoscope 24, adjacent to the viewing port 26. In this example, the scope 24 is a lateral viewing scope in which the field of view is to the side and thus the LED array 20 is also arranged to direct light to the side. It will be apparent that, although the array 20 is shown positioned distally of the viewing port 26 it could also be positioned proximally.

To dissipate any heat generated by the array 20, a heat sink and cooling means, such as fins (not shown) may be provided on the substrate 12 of the array 20 and/or a portion 28 of the insertion tube 22 on which the substrate 12 itself is mounted.

Figure 3:
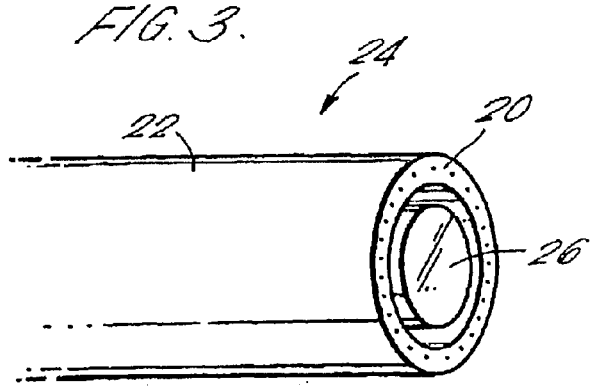
FIG. 3 illustrates a perspective view of a second embodiment of the invention, also with the array at the distal end.

In a second embodiment shown in FIG. 3 a forward viewing scope 24 is provided with a viewing port 26 providing a field of view in the direction of the longitudinal axis of the insertion tube 22. In this case, the LED array 20 may conveniently be in annular form, surrounding the viewing port 26.

Figure 4:
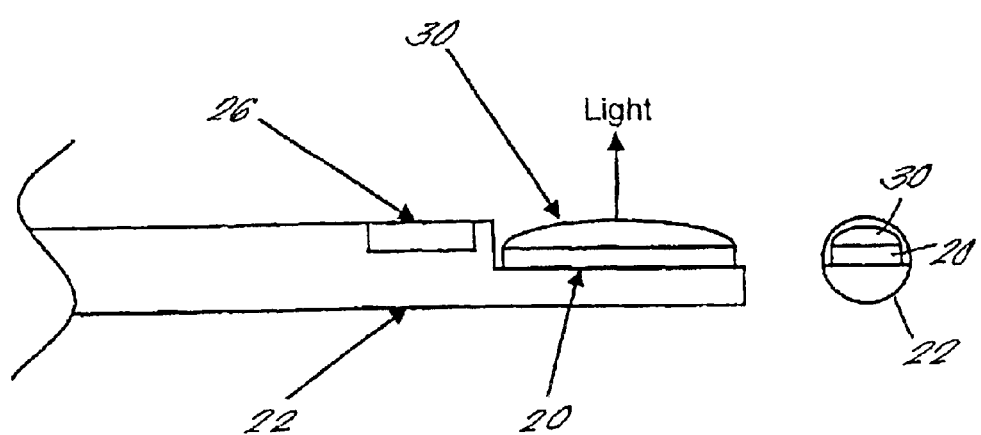
FIG. 4 illustrates a side and end view of a third embodiment of the invention, also with the array at the distal end.

It may be desirable to focus the light produced by the array 20. Focussing can be achieved in a number of ways. As shown in FIG. 4, the protective layer of optically clear glue 18 which covers the LED chips 10 may be shaped to act as a lens 30.

Figure 5:
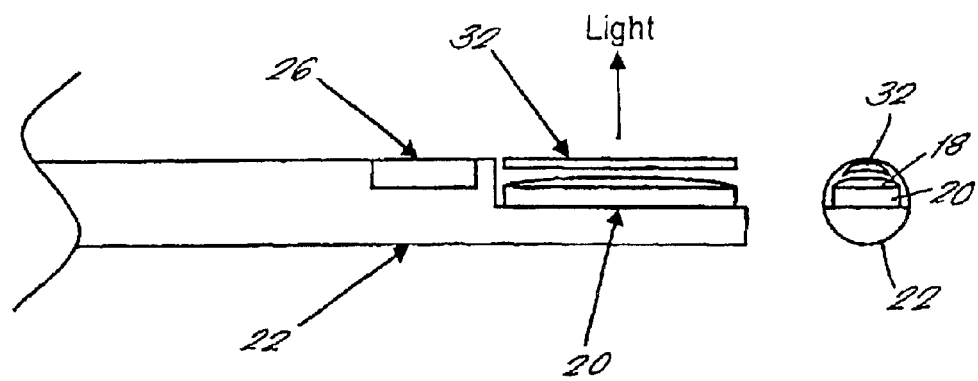
FIG. 5 illustrates a side and end view of a fourth embodiment of the invention, also with the array at the distal end.

Alternatively, as shown in FIG. 5, a separate lens 32 may be provided in front of the array 20. Although not illustrated, either of these focussing methods can be incorporated in the forward viewing embodiment as shown in FIG. 3.

Figure 6:
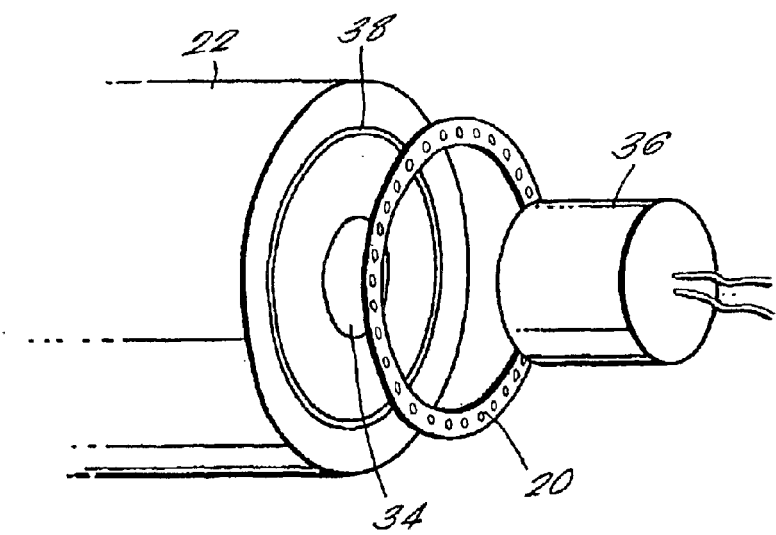
FIG. 6 illustrates a perspective view of a fifth embodiment of the invention, with the array at the proximal end of the borescope or endoscope.

In some cases, it may be preferred not to place the array 20 at the distal end of the scope 24 but at the proximal end. One example of such an arrangement is illustrated in FIG. 6 which shows the proximal end of scope 24. In this embodiment, an optical train 34, e.g. a series of lenses, transmits an image from the distal end (not shown) of the scope 24 to the proximal end and onto, in this case, a camera attachment 36 (or an eyepiece assembly for direct viewing).

To illuminate the field of view, a bundle of optical fibres 40 is provided in annular form extending along the scope 24 surrounding and concentric with the optical train 34. Thus, the fibres present an annular end face 38 at the proximal end of the scope 24. To provide illumination, an annular LED array is provided adjacent to the end face 38. As shown, the substrate 12 of the array 20 is also annular to allow the camera attachment 36 or eyepiece components etc to be positioned aligned with the optical train 34.

Figure 7:
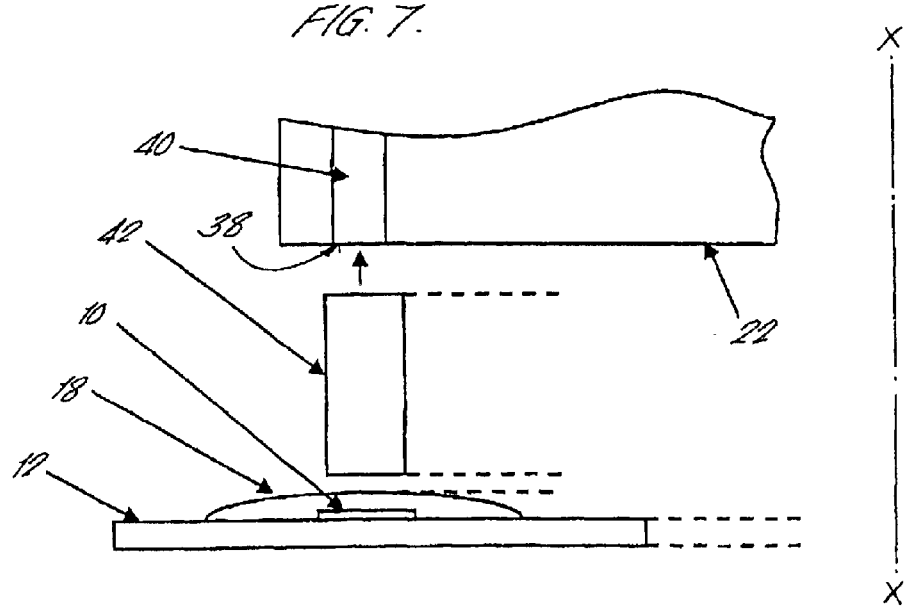
FIG. 7 illustrates a cross sectional view of a sixth embodiment of the invention, with the array at the proximal end.

An annular light pipe 42 may be provided between the array 20 and the end face 38 as shown in FIG. 7 to collect light produced by the array 20 and transmit it to the fibres 40. FIG. 7 (and FIGS. 8–11) shows one side of the proximal end of the scope, the other side corresponding so as to be symmetrical about the longitudinal axis X—X of the tube 22. A light pipe 42 usually consists of a hollow tube of optical grade material such as plastic or glass which transmits light with very few losses due to total internal reflection.

Figure 8:
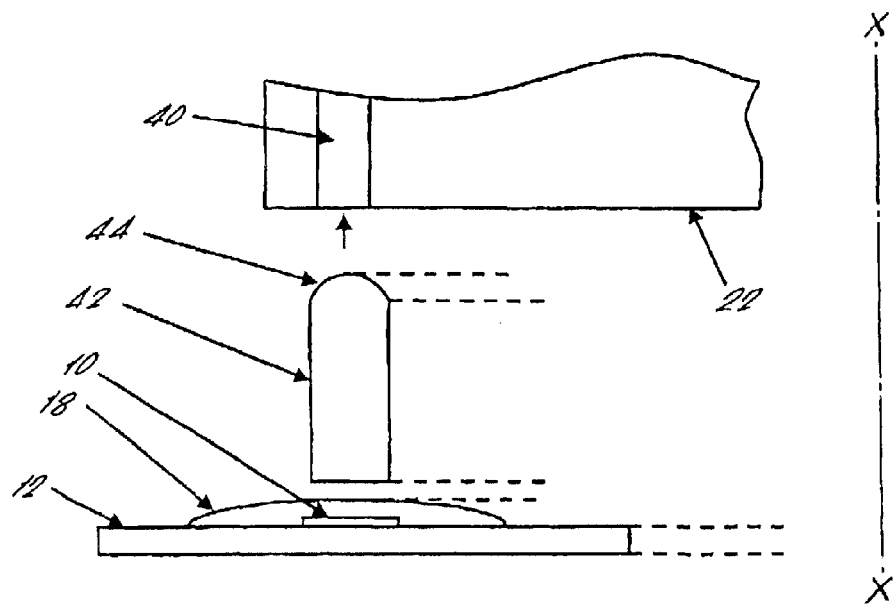
FIG. 8 illustrates a cross sectional view of a seventh embodiment of the invention, with the array at the proximal end.

The distal end of the light pipe 42 may be shaped to form a lens 44 as seen in FIG. 8, in order to focus the light onto the end face 38 of the fibres. Alternatively, a separate focussing ring lens 32 may be provided between the light pipe 42 and the end face 38 as seen in FIG. 9.

As another alternative, the light pipe 42 may be dispensed with altogether and a separate ring lens 32 alone may be provided between the array 20 and the end face 38 as shown in FIG. 10.

Another possibility is for the protective layer 18 of the array 20 to be shaped so as to form a focussing lens 30, as shown in FIG. 11.

In the embodiments of FIGS. 6–11, the LED chips 10 are typically arranged in a single circle with the diameter of a circle running through the centres of the chips in the order of 15 mm. The array preferably includes at least 50 and more preferably between 80 and 90 LEDs. Each LED chip 10 is typically in the order of 0.3 mm sq.

The LED chips 10 used in, the array 20 may be those which emit white light from the semi-conductor itself. Alternatively, LED chips 10 which produce blue light can be used, in which case white or yellow phosphor is incorporated in the protective shield 18 with the result that the white light is emitted from the array 20 overall.

It is also possible to use a mixture of red, green and blue LEDs on the same substrate 12 which act in combination to provide white light from the array 20 as a whole. Using red, green and blue LEDs also provides the possibility of strobing the light. In some conventional endoscope systems it is known to use a white light source with a rotating filter wheel carrying red, green and blue filters positioned between the light source and the optical fibres. The result is that light transmitted from the end of the scope over the field of view alternates between red, green and blue. A monochrome camera is then used to gather an image of the field of view and a special processor converts the picture provided by the camera into colour. This known arrangement provides very high resolution pictures with good colour, but requires sufficient space to accommodate the filter wheel and motor as well as complicated synchronisation circuitry. It is therefore relatively expensive.

In the present invention, the filter wheel, drive motor and synchronisation circuitry can be avoided by using red, green and blue LEDs which are strobed, i.e. operated sequentially, typically about 50 Hz, by a specialised power supply system. As before, this provides alternating red, green and blue light at the distal end of the scope and a monochrome camera and suitable processor can be used to provide full colour images. This arrangement is cheaper and more compact than the prior art and usually produce better colours and resolution than a system using white light and a colour imager.

Other types LED could also be employed. For example, LED chips 10 producing infra red light could be used to form a type of thermal image with appropriate specialised image equipment. Alternatively, LED chips 10 producing ultraviolet light could be employed to allow the use of the borescope or endoscope in dye penetrant and magnetic particle testing.

In those embodiments in which the array 20 is provided at the proximal end of the scope, the array and focussing lens or light pipe etc may be included as an integral part of the scope 24. Alternatively, they may be provided as components in a separate module which is detachable from the scope 24 as required.

As those skilled in the art will appreciate, the present invention provides an improved arrangement for providing illumination via a borescope or endoscope, which reduces light losses, is very compact and does not interfere with positioning of the other components in the scope. It will be apparent that a number of variations and modifications may be made to the particular embodiments described, without departing from the scope of the present invention.

What is claimed is:

1. Apparatus for use as a borescope or endoscope for viewing an object at a remote or inaccessible location, comprising a tube having a proximal end and a distal end, means in the tube for obtaining an image of an object and transmitting it to a viewing device, and illumination means comprising an array of light emitting diodes (LEDs) mounted on a substrate and encased in a common protective shield of optically clear material, wherein the illumination means further comprises a plurality of optical fibres for transmitting light through the tube from the proximal end to the distal end, wherein the fibres are arranged in annular form and present an annular end face at the proximal end of the tube, and wherein the array of light emitting diodes is annular and is positioned at the proximal end of the tube facing the annular end face of the fibres, and wherein an annular light pipe is positioned between the annular array and the annular end face for transmitting light from the array to the optical fibres.

2. Apparatus as claimed in claim 1, wherein the protective shield is shaped to form a lens to focus light produced by the LEDs.

3. Apparatus as claimed in claim 1, wherein a lens is positioned in front of the array to focus light produced by the LEDs.

4. Apparatus as claimed in claim 1, wherein the proximal end of the light pipe is shaped so as to form a lens to focus light onto the end face of the fibres.

5. Apparatus as claimed in claim 1, wherein a separate lens is positioned between the light pipe and the end face of the fibres to focus light onto the end face.

6. Apparatus as claimed in claim 1, further comprising cooling means to dissipate heat produced by the array.

7. Apparatus as claimed in claim 1, wherein the LEDs emit white light.

8. Apparatus as claimed in claim 1, wherein the LEDs emit blue light and the protective shield incorporates white or yellow phosphor whereby the array produces white light.

9. Apparatus as claimed in claim 1, wherein the array comprises LEDs emitting different colours, operable in combination to produce white light.

10. Apparatus as claimed in claim 9, wherein the array includes LEDs operable to produce red, green and blue light and means to operate the LEDs sequentially so as to provide light which sequentially alternates between red, green and blue.

11. Apparatus as claimed in claim 1 wherein the LEDs produce infra-red light.

12. Apparatus as claimed in claim 1 in which the LEDs produce ultra-violet light.

13. Apparatus as claimed in claim 1, wherein the array includes at least 50 LEDs.

14. Apparatus as claimed in claim 1, wherein the array includes at least 80 LEDs.

15. Apparatus as claimed in claim 2 wherein the lens is in the form of a built up mound of protective shield material having a curved, lens forming upper surface.

* * * * *